United States Patent
Bron et al.

[11] Patent Number: 5,378,718
[45] Date of Patent: Jan. 3, 1995

[54] 1,4-DIHYDROPYRIDINE DERIVATIVES

[75] Inventors: Jan Bron, Giessenburg; Geert J. Sterk, Utrecht; Hendrik Timmerman, Voorschooten; Jan F. Van Der Werf, Amsterdam, Netherlands

[73] Assignee: Cedona Pharmaceuticals B.V., Haarlem, Netherlands

[21] Appl. No.: 965,270

[22] PCT Filed: Jul. 31, 1991

[86] PCT No.: PCT/EP91/01442

§ 371 Date: Jan. 22, 1993

§ 102(e) Date: Jan. 22, 1993

[87] PCT Pub. No.: WO92/02503

PCT Pub. Date: Feb. 20, 1992

[30] Foreign Application Priority Data

Aug. 2, 1990 [NL] Netherlands ............... 9001752

[51] Int. Cl.⁶ .............. C07D 211/86; A61K 31/455
[52] U.S. Cl. .......................... 514/356; 546/321
[58] Field of Search ................... 546/321; 514/356

[56] References Cited

U.S. PATENT DOCUMENTS

| | | | |
|---|---|---|---|
| 4,472,411 | 9/1984 | Hatayama et al. | 424/266 |
| 4,772,612 | 9/1988 | Goldmann et al. | 514/302 |
| 4,992,451 | 2/1991 | Koike et al. | 514/318 |

FOREIGN PATENT DOCUMENTS 0114270  8/1984  European Pat. Off. .
1173862 12/1969  United Kingdom .
1455502 11/1976  United Kingdom .

OTHER PUBLICATIONS

Appel Current Neurology vol. 6, p. 108 Year Book Medical Publishers, Inc. 1987.
Schramm et al. Nature vol. 303, pp. 535–537, Jun. 1983.
Bossert et al. Angew, Chem. Int. Ed. Engi. 20, 762–769, 1981.

*Primary Examiner*—Jane T. Fan
*Attorney, Agent, or Firm*—Jacobson, Price, Holman & Stern

[57] ABSTRACT

Compounds a formula (I)

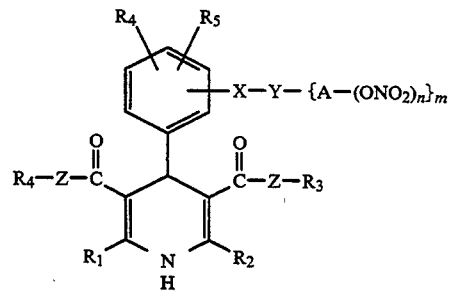

wherein the substituents and symbols have the meanings given in the specification, are new compounds with marked cardiovascular activity.

5 Claims, 2 Drawing Sheets

1,4-DIHYDROPYRIDINE DERIVATIVES

The invention relates to novel 4-(substituted phenyl)-1,4-dihydropyridine derivatives containing one or more nitrate ester functions in at least one of the substituents on the phenyl ring, and to their salts. These novel compounds have the formula 1 (cf. enclosed formulae sheet), wherein $R_1$ represents a lower alkyl group, $R_2$ represents a lower alkyl group or —$CH_2$—S—$CH_2$—$CH_2$—$NH_2$, $R_3$ and $R_4$ independently represent a lower, optionally branched (bi)(cyclo)alkyl group, $R_5$ and $R_6$ independently represent H, a lower, optionally branched alkyl group, a lower, optionally branched alkoxy group, CN, $NO_2$, F, Cl or Br, X represents O, NH, CO, —O($CH_2$)$_p$—CO— or S, Y represents O, N, NH, S, CO, CONH, $CO_2$ or a bond, with the provisos that X and Y do not at the same time represent O and/or S, Y does not represent O, NH or S, when X is NH, Y does not represent CO, $CO_2$ or CONH, when X is CO, and Y does not represent N, NH, CONH or $CO_2$, when X is O, A represents an optionally branched (bi)(cyclo)alkylene group, or a group of the formula [($CH_2$)$_2$O]$_q$($CH_2$)$_2$, wherein q is 1 or 2, n and m independently are 1, 2 or 3, Z represents O or NH and p is 1–6.

It has been found that these novel 1,4-dihydropyridine derivatives have valuable properties for use as medicaments. They can be used, optionally symptomatically, in the treatment of pathological processes in mammals, especially man, where it is necessary, for example, a. to increase the availability of oxygen to the tissues;

b. to protect the mucosa, for example the gastrointestinal mucous membrane;

c. to intervene in the reproduction mechanisms of viruses; or d. to reduce resistance to oncolytic agents and thus to maintain the oncolytic activity.

By virtue of their pharmacological characteristics, the novel 1,4-dihydropyridine derivatives are, for example, suitable for use as medicaments, for example in the treatment and/or prevention of a) ischemic heart diseases (such as angina pectoris and latent ischemia)

b) cardiac decompensation, myocardial infarction or raised blood pressure (especially portal hypertension)

c) cerebral thrombosis and atherosclerosis d) vessel spasms and arrhythmia etc.

e) disorders of the gastrointestinal tract, such as achalasia and irritable bowel syndrome f) tardive dyskinesia.

The invention thus also relates to a medicament for the treatment of the abovementioned disorders which contains, as active substance, a 1,4-dihydropyridine derivative of the formula 1 described above and/or a pharmacologically compatible salt thereof.

1,4-Dihydropyridine derivatives are described in many patents, for example in British Patents 1,173,862 and 1,455,502 and U.S. Pat. No. 4,472,411. The compounds described in these literature references are known to have a calcium influx-modulating action which is used in particular in the therapy of ischemic heart diseases, hypertension and cerebral circulatory disturbances.

These known 1,4-dihydropyridine derivatives generally have in common that they have a 4-(nitrophenyl)2,6-dimethyl-1,4-dihydropyridine-3,5-dicarboxylic acid ester structure. It is also known that organic nitrate esters can be used in ischemic heart diseases and cardiac decompensation. Organic nitrate esters such as glyceryl trinitrate and isosorbide dinitrate have already been used medicinally for more than 100 years and 50 years respectively.

With regard to the manner in which vasodilation is effected by nitrate esters it is postulated that this is caused, inter alia, by nitric oxide NO. It is known that endogenous NO can be liberated from endothelial cells of an intact vessel wall by specific mediators, such as acetylcholine, bradykinin, serotonin, histamine and the like. This endogenous NO, which is also termed Endothelium Derived Relaxing Factor (EDRF), is alleged, in turn, to stimulate the enzyme guanylate cyclase in the adjacent smooth muscle cells. As a result, inter alia, of the increased concentrations of cyclic GMP, the existing balance in the vessel wall tension is disturbed, which, via a cascade of reactions, ultimately leads to relaxation of the smooth muscle cells in the vessel wall.

Organic nitrate esters can give rise to vasodilation even if the endothelial cell layer has been damaged or removed, which effect could be explained by direct formation of NO from these nitrate esters.

From the therapeutic standpoint it can be worthwhile to combine medicaments, such as Ca-antagonists and organic nitrate esters, in dosages at which possible side effects are prevented as far as possible and, nevertheless, a clinically optimum result is obtained. A chemical combination can be produced under certain circumstances, but it is then unpredictable as to what the pharmacological and clinical characteristics of such compounds will be.

Thus, it is known, from European Patents 207,674 and 114,270, inter alia, that these 1,4-dihydropyridine-3,5-dicarboxylic acids can be esterified with the free hydroxyl groups of known organic nitrate esters, such as glycerol mononitrate, glycerol dinitrate or isosorbide mononitrate. In European Patent 207,674 the 2—$CH_3$— group of nifedipine (described in British Patent 1,173,862) is replaced by a 2—$NH_2$— group in order to achieve a good Ca-antagonistic activity. The esterification takes place at C3 and/or C5 with nitroxy-alkanol derivatives.

The hypotensive action of a number of compounds described in this Patent is alleged to be equal to that of nifedipine, the onset of action, however, alleged to be slower than that of nifedipine. Quantitative examples of this activity are, however, not given. This literature reference gives no teaching with regard to the influence on the contractility in vivo.

European Patent 114,270 esterifies at C5 of the 1,4-dihydropyridine ring, inter alia with isosorbide mononitrate.

The compounds concerned here are alleged to have an action on the blood circulation and, for example, it is alleged that they can be used as an anti-hypertensive agent or a coronary therapeutic agent. Because the compounds concerned here are hybrid compounds of organic nitrate esters and Ca-modulating 1,4-dihydropyridines, this is possibly to be expected but is not convincingly backed up by experiment. Actually the compounds described in European Patents 114,270 and 207,674 must be regarded as prodrugs of fixed combinations of compounds which are known per se and have either Ca-antagonistic activity or nitrate activity.

In the case of the 1,4-DHP esters described in European Patents 206,674 and 114,270 it is then, incidentally, to be expected that after conversion of the 3- and/or 5-ester to the corresponding carboxylic acid or carboxylic acids, compounds which do not have a particularly high hemodynamic activity will remain, that is to say glyceryl dinitrates and glyceryl mononitrates, isosorbide mononitrate and the inactive 1,4-DHP-carboxylic acids.

The 1,4-dihydropyridine derivatives of the invention also contain one or more organic nitrate ester groups, but in these derivatives the 1,4-dihydropyridine skeleton of, for example, the abovementioned British Patents 1,173,862 and 1,455,502 and U.S. Pat. No. 4,472,411 is left intact.

In fact, it has been found that incorporation of one or more nitrate ester groups in 1,4-dihydropyridine derivatives in order to obtain a potent Ca-modulating activity and a high vasodilatory (nitrate) activity can be achieved by introducing one or more optionally branched (bi)(cyclo)alkylene groups, which are substituted by one or more nitrooxy groups, as substituents on the aryl ring of 4-(phenyl)-1,4-dihydropyridine derivatives.

Preferred compounds according to the invention are those of the general formula 1, wherein
$R_1$ represents a 1-4C-alkyl group,
$R_2$ represents a 1-4C-alkyl group,
$R_3$ and $R_4$ independently represent a 1-4C-alkyl group or a menthyl group,
$R_5$ represents H, 1-4C-alkoxy, $NO_2$, Cl or Br,
$R_6$ represents H,
X represents O, CO or $-O(CH_2)_p-CO-$,
Y represents N, NH, CO or a bond,
A represents an optionally branched 2-15C-alkylene group, a dimethylene cyclohexane group, a cyclohexane-1,2-ylene group or a group of the formula $[(CH_2)_2O]_q(CH_2)_2$, wherein q is 1 or 2,
n is 1,
m is 1 or 2,
Z represents O and
p is 1,
and their salts.

Particularly preferred compounds according to the invention are those of the general formula 1, wherein
$R_1$ represents a 1-4C-alkyl group,
$R_2$ represents a 1-4C-alkyl group,
$R_3$ and $R_4$ independently represent a 1-4C-alkyl group,
$R_5$ represents H, 1-4C-alkoxy, $NO_2$, Cl or Br,
$R_6$ represents H,
X represents O,
Y represents a bond,
A represents an optionally branched 2-15C-alkylene group, a dimethylene cyclohexane group or a group of the formula $[(CH_2)_2O]_q(CH_2)_2$, wherein q is 2,
n is 1,
m is 1 and
Z represents O,
and their salts.

The pharmacological experiments which were carried out using the novel 1,4-dihydropyridine derivatives in vitro (and in vivo) demonstrate that under various experimental conditions there is both a powerful Ca-modulating activity and relaxant (nitrate) activity. Thus, for example, in an experiment in which a rat aorta is contracted using phenylephrine, the novel compounds, in contrast to the pure Ca-antagonist nifedipine, are able to effect 100% relaxation of this contraction, which indicates additional nitrate activity.

The medicaments of the invention can have all conventional pharmaceutical forms and are prepared in the customary ways.

The synthesis of the novel compounds takes place by methods known per se. A number of these syntheses are shown in the appended reaction schemes A-H. In these reaction schemes, $R_5$ and $R_6$ have the same meaning as in formula 1. $R_7$ is formyl group or a 1,4-dihydropyridine group, or a group which can simply be converted to a formyl group or a 1,4-dihydropyridine group. $R_8$ is a hydroxyl group or a hydroxyl group esterified with nitric acid.

BRIEF DESCRIPTION OF DRAWING

Reaction Scheme A

In reaction scheme A X is a sulfur or oxygen atom and $R_9$ is a detachable group, such as a chlorine, bromine or iodine radical or a sulfonic acid ester group, and the like.

Figure 1:
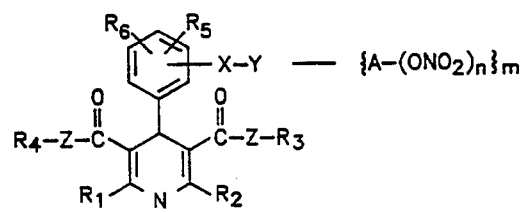
Figure 2A:
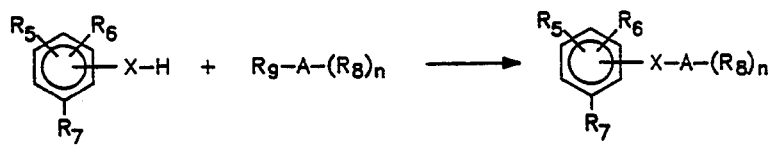
Figure 2B:
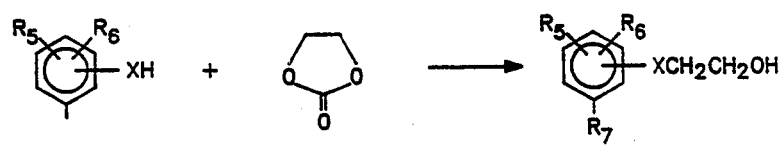
Figure 2C:
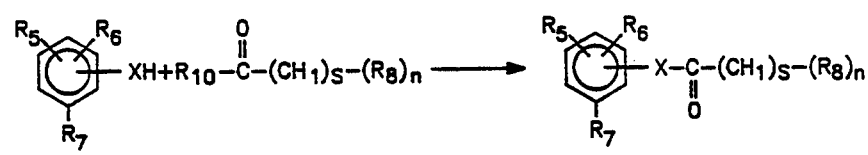
Figure 2D:
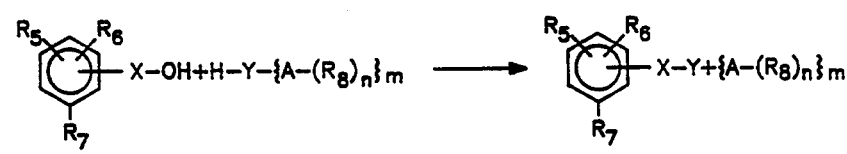
Figure 2E:
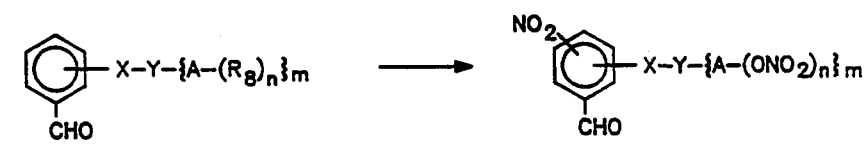
Figure 2F:
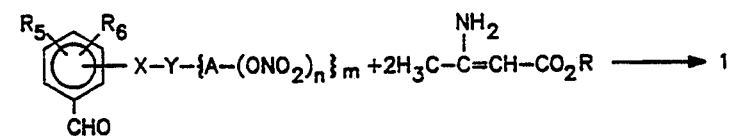
Figure 2G:
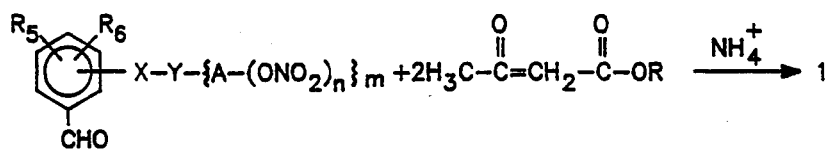
Figure 2H:
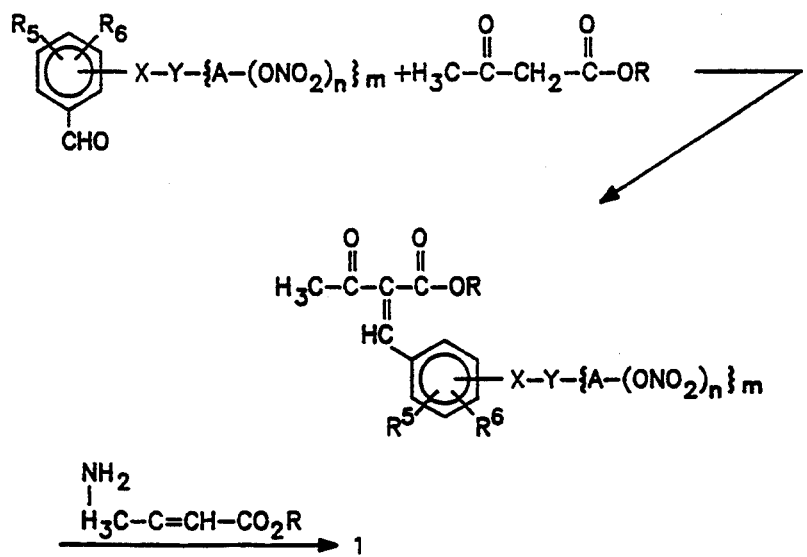

This reaction can be carried out in a polar solvent, such as water methanol, ethanol, propan-2-ol, dimethylformamide, tetrahydrofuran and the like. The reaction proceeds under the influence of a base, such as sodium methanolate, sodium hydride, sodium amide, potassium carbonate and the like. The reaction temperature can vary from $-20°$ C. to $+160°$ C. If $R_8$ in this scheme is a hydroxyl group, the compound can be converted in a known manner to a nitrate ester.

Scheme B

In reaction scheme B X can be an oxygen or sulfur radical, a carboxyl group or a group having the general formula $O-(CH_2)_p-CO_2$.

In the presence of a quaternary ammonium compound or a strong base, the starting compound in scheme B can react with ethylene carbonate to form a hydroxyethyl ester or hydroxyethyl ether. A hydroxy compound of this type can be converted in a known manner to a nitrate ester.

Scheme C

In reaction scheme C X represents an oxygen or sulfur radical or an imino group and s is 1-6.

In the condensation reaction of scheme C, $R_{10}$ represents a chlorine or bromine radical or a hydroxyl group, on condition that if $R_{10}$ is a hydroxyl group this group must be "activated" by a carbodiimide or a chloroformic acid ester before the reaction can proceed.

The reaction can be carried out in a solvent, such as dimethylformamide, acetonitrile, tetrahydrofuran, dioxane, ethyl acetate, pyridine, dichloromethane and the like.

Scheme D

In reaction scheme D X is a C=O group or a group having the general formula $-O-(CH_2)_p-CO-$ and Y is an oxygen radical or an imino group.

Suitable solvents for this reaction are, for example, dimethylformamide, tetrahydrofuran, dichloromethane, pyridine, ethyl acetate, chloroform, acetonitrile, dioxane and the like.

Before the reaction can proceed, the carboxyl group of the starting compound must be converted to an acid chloride or acid bromide, or be activated, for example by means of a carbodiimide or a chloroformic acid ester.

Scheme E

In reaction scheme E X represents an oxygen radical or a group having the general formula —O—($CH_2$)$_p$—CO— and Y represents a bond or an imino group.

In the reaction of scheme E, the aldehyde is added slowly to absolute nitric acid at a temperature of between −20° C. and +20° C. Under these conditions an aromatic nitro compound is obtained. The aromatic nitration preferably takes place at the p-position relative to the alkoxy group.

If $R_8$ represents an alcohol function, this function will be converted under these conditions to a nitric acid ester. If several nitro compounds are formed during this reaction, the products can be separated from one another by means of crystallization and/or chromatographic methods.

Schemes F, G and H

A number of syntheses for the preparation of Hantzsch esters, as described in the literature, are shown in reaction schemes F, G and H.

The following examples illustrate the preparation of the compounds of the invention.

EXAMPLE I 3,5-Diethoxycarbonyl-2,6-dimethyl-4-[4-(3-nitroxypropyl)carbonyloxy]phenyl-1,4-dihydropyridine 1.8 g of $PCl_5$ were added at room temperature, under nitrogen, to a stirred solution of 1.3 g of 4-nitroxybutyric acid in 100 ml of dichloromethane. After one hour the solution was evaporated and the residue was added to a solution of 1.5 g of 3,5-diethoxycarbonyl-2,6-dimethyl-4-(4-hydroxyphenyl)-1,4-dihydropyridine and 1.5 g of 4-dimethylaminopyridine in dichloromethane. The resulting solution was refluxed for 6 hours, after which the reaction mixture was washed successively with dilute hydrochloric acid and a sodium carbonate solution. After drying over sodium sulfate, the solution was evaporated and the residue was purified by column chromatography (silica gel, dichloromethane:diethyl ether 3:1).

Yield 6%. Empirical formula $C_{23}H_{28}N_2O_9$. Molecular weight 476. Melting point 95°–98° C. TLC system: ethyl acetate:petroleum ether 60-80/1:1. $R_f$ 0.49.

NMR data: ($CDCl_3$): 1.22 ppm, t, J=7.3 Hz, 6.0H (ethyl-$CH_3$); 2.16 ppm, q, J=6.7 Hz, 2.0H (C—$CH_2$—C); 2.32 ppm, s, 6.0H (dihydroxypyridyl—$CH_3$, 2x); 2.69 ppm, t, J=6.0 Hz, 2.0H ($CH_2$—O); 4.09 ppm, q, J=7.3 Hz, 4.0H (ester $CH_2$); 4.58 ppm, t, J=6.0 Hz, 2.0H ($CH_2ONO_2$); 5.00 ppm, s, 1.0H (CH); 5.75 ppm, s, 0.8H (NH); 6.92 ppm, d, J=8.6 Hz, 2.0H (arom. H); 7.32 ppm, d, J=8.6 Hz, 2.0H (arom. H)

EXAMPLE II 3,5-Dimethoxycarbonyl-2,6-dimethyl-4-[4-[(2-nitroxyethyl)aminocarbonyl]phenyl]-1,4-dihydropyridine 1 ml of ethyl chloroformate was added at −10° C. to a solution of 2 g of 4-(4-carboxyphenyl)-3,5-dimethoxycarbonyl-2,6-dimethyl-1,4-dihydropyridine and 1.27 ml of triethylamine in $CH_2Cl_2$. After everything had been added, the solution was stirred for a further 45 minutes. 1.6 g of aminoethyl nitrate×$HNO_3$ was added, followed by the addition of 2.75 ml of triethylamine. The resulting mixture was stirred for a further 15 hours at room temperature. After the reaction mixture had been washed successively with dilute hydrochloric acid and a solution of sodium carbonate, the solution was dried over sodium carbonate and evaporated. The residue was crystallized from ethyl acetate/petroleum ether (60°–80°).

Yield 45%. Empirical formula $C_{20}H_{23}N_3O_8$. Molecular weight 433. Melting point 112°–116° C. TLC system: ethyl acetate. $R_f$ 0.67

NMR data: ($CDCl_3$): 2.33 ppm, s, 6.2H (2×$CH_3$-dihydropyridine); 3.61 ppm, s, 6.0H (2×$CH_3CO$); 3.77 ppm, q, J=5.1 Hz, 2.0H ($CH_2$—N); 4.62 ppm, t, J=5.1 Hz, 2.0H ($CH_2$—O); 5.03 ppm, s, 1.0H (CH); 6.13 ppm, s, 1.0H (NH of dihydropyridine); 6.52 ppm, broad signal, 1.0H (CONH); 7.30 ppm, d, J=7.6 Hz, 2.0H (arom. H); 7.58 ppm, d, J=7.6 Hz, 2.0H (arom. H)

EXAMPLE IIIa 2-(3,5-Dimethoxycarbonyl-2,6-dimethyl-1,4-dihydropyridin-4-yl)phenoxyacetic Acid A solution of 5 g of 2-formylphenoxyacetic acid and 6.4 g of methyl 3-aminocrotonate in methanol was refluxed for 24 hours and evaporated. The residue was dissolved in a solution of sodium carbonate in water. This solution was washed twice with ethyl acetate and acidified to pH 2 with dilute hydrochloric acid, after which the solution was again extracted with ethyl acetate. The organic layer was dried over magnesium sulfate and evaporated. The residue was crystallized from ethyl acetate/petroleum ether 60-80.

Yield 24%. Melting point 185°–190° C.

1H-NMR ($CDCl_3$): 2.32 ppm, s, 6.0H (2×$CH_3$ dihydropyridine); 3.60 ppm, s, 6.0H (2×$CH_3O$); 4.70 ppm, s, 2.0H ($CH_2$); 5.44 ppm, s, 0.9H, (CH); 6.20 ppm, s, 0.9H (NH); 6.60–7.40 ppm, 5.0H (arom. H+$CO_2H$).

EXAMPLE III 3,5-Dimethoxycarbonyl-2,6-dimethyl-4-[2-[(2-nitroxyethyl)aminocarbonylmethoxy]phenyl]-1,4-dihydropyridine 1.4 ml of ethyl chloroformate were added at 0° C. to a solution of 4.8 g of 2-(3,5-dimethoxycarbonyl-2,6-dimethyl-1,4-dihydropyridin-4-yl)phenoxyacetic acid and 1.84 ml of triethylamine in $CH_2Cl_2$. The solution was stirred for 30 minutes, after which a solution of 2.25 g of aminoethyl nitrate×$HNO_3$ and 1.84 ml of triethylamine in $CH_2Cl_2$ was added. After stirring for 10 minutes, the organic layer was washed with dilute acid and base, dried over $MgSO_4$ and evaporated. The residue was washed with ether and dried.

Yield 15%. Empirical formula $C_{21}H_{25}N_3O_9$. Molecular weight 463. Melting point 160°–162° C. TLC system: ethyl acetate $R_f$ 0.73.

NMR data: ($CDCl_3$): 2.31 ppm, 6.0H (2×$CH_3$); 3.53–3.82 ppm, m, 8.0H (2×$OCH_3$, $CH_2N$); 4.45–4.68 ppm, m, 4.0H (2×$CH_2O$); 5.42 ppm, s, 0.9H (CH); 5.69 ppm, s, 0.9H (NH); 6.60–7.35 ppm, m, 4.0H (arom. H); 8.50 ppm, bs, 0.9H (CONH).

EXAMPLE IV 4-(2-[[2,2-Bis-(nitroxyethyl)]aminocarbonyl]phenyl)-3,5-dimethoxycarbonyl-2,6-dimethyl-1,4-dihydropyridine Prepared as described under Example III from the compound of Example IIIa and diethanolamine dinitrate ester×HNO$_3$.

Yield 44%. Empirical formula C$_{23}$H$_{28}$N$_4$O$_{12}$. Molecular weight 552. Melting point 97°–98° C. TLC system: ethyl acetate. R$_f$: 0.60.

NMR data: (CDCl$_3$): 2.30 ppm, s, 6.0H (2×CH$_3$); 3.58 ppm, s, 6.0H (2×OCH$_3$); 3.79 ppm, t, J=5.2 Hz, 2.0H (CH$_2$N); 4.04 ppm, t, J=5.2 Hz, 2.0H (CH$_2$N); 4.58–4.81 ppm, m, 4.0H (2×CH$_2$O); 5.29 ppm, s, 1.0H (CH), 5.68 ppm, s, 0.9H (NH); 6.70–7.33 ppm, 4.0H (arom. H)

EXAMPLE V 3,5-Dimethoxycarbonyl-2,6-dimethyl-4-[3-[(2-nitroxyethyl)aminocarbonyl)phenyl]-1,4-dihydropyridine Prepared from 4-(3-carboxyphenyl)-3,5-dimethoxycarbonyl-2,6-dimethyl-1,4-dihydropyridine as described in Example III.

Yield 28%. Empirical formula C$_{20}$H$_{23}$N$_3$O$_8$. Molecular weight 433. Melting point 116°–119° C. TLC system: ethyl acetate. R$_f$: 0.72.

NMR data: (CDCl$_3$): 2.28 ppm, s, 6.0H (2×CH$_3$); 3.62 ppm, s, 6.0H (2×OCH$_3$); 3.78 ppm, q, J=5.3 Hz, 2.0H (NCH$_2$); 4.64 ppm, t, J=5.3 Hz, 2.0H (CH$_2$O); 5.04 ppm, s, 1.0H (CH); 6.11 ppm, s, 0.9H (NH); 6.64 ppm, bs, 1.0H (CONH); 7.14–7.78 ppm, m, 4.0H (arom. H)

EXAMPLE VIa 3-(2-Hydroxyethoxy)benzaldehyde 1.42 g of sodium were dissolved in 200 ml of ethanol. 7.5 g of 3-hydroxybenzaldehyde and 10.5 g of bromoethanol were added and the resulting solution was refluxed for 5 hours. The solution was purified by column chromatography (silica, CH$_2$Cl$_2$).

EXAMPLE VIb 3-(2-Nitroxyethoxy)benzaldehyde

A solution of 5 g of the compound from Example VIa in ethyl acetate was added slowly at 0° C. to a mixture of 3.8 ml of HNO$_3$ and 13 ml of acetic anhydride. After everything had been added, the mixture was poured into water, the resulting mixture was stirred for 30 minutes and extracted with ethyl acetate and the extract was washed with sodium carbonate, dried over MgSO$_4$ and evaporated.

1H-NMR (CDCl$_3$): 4.30 ppm, t, J=4.5 Hz, 2.0H (OCH$_2$); 4.84 ppm, t, J=4.5 Hz, 2.0H (CH$_2$ONO$_2$): 7.06–7.80 ppm, m, 4.0H (arom. H); 9.93 ppm, s, 0.9H (CH)

EXAMPLE VI 3,5-Dimethoxycarbonyl-2,6-dimethyl-4-[3-(2-nitroxyethoxy)phenyl]-1,4-dihydropyridine A solution of 2.0 g of the compound from Example VIb and 2.2 g of methyl 3-aminocrotonate in 100 ml of methanol was refluxed for 170 hours. After evaporation, the residue was washed with ether and then crystallized from ethyl acetate/petroleum ether 60-80.

Yield 22%. Empirical formula C$_{19}$H$_{22}$N$_2$O$_6$. Molecular weight 406 Melting point 154°–157° C. TLC system: diethyl ether R$_f$: 0.75

NMR data: (CDCl$_3$): 2.31 ppm, s, 6.0H (2×CH$_3$); 3.66 ppm, s, 6.0H (2×OCH$_3$); 4.17 ppm, t, J=5.2 Hz, 2.1H (OCH$_2$); 4.77 ppm, t, J=5.2 Hz, 1.9H (CH$_2$ONO$_2$); 4.97 ppm, s, 0.9H (CH); 4.97 ppm, s, 1.1H (NH); 6.56–7.26 ppm, m, 4.0H (arom. H).

EXAMPLE VIIa 2-(2-Hydroxyethoxy)benzaldehyde

A mixture of 0.2 mol of 2-hydroxybenzaldehyde, 0.2 mol of ethylene carbonate and 0.3 mol of tetraethylammonium bromide was heated at 140° C. for 2 hours. After cooling, the reaction mixture was taken up in ethyl acetate, washed with water, dried over MgSO$_4$ and evaporated. The compound was purified by distillation.

Yield 70%. Boiling point 141°–144° C. (0.1 mm Hg).

1H-NMR (CDCl$_3$); 2.90 ppm, t, J=5.0 Hz, 1.0H (OH); 3.96–4.23 ppm, m, 4.0H (2×CH$_2$); 6.90–7.90 ppm, m, 4.0H (arom. H): 9.94 ppm, s, 0.9H (CH).

EXAMPLE VIIb 2-(2-Nitroxyethoxy)benzaldehyde

A solution of 5 g of the compound from Example VIIa in ethyl acetate was added slowly at 0° C. to a mixture of 3.8 ml of HNO$_3$ and 13 ml of acetic anhydride. After everything had been added, the mixture was poured into water, the resulting mixture was stirred for 30 minutes and extracted with ethyl acetate and the extract was washed with sodium carbonate, dried over MgSO$_4$ and evaporated.

Yield 80%.

1H-NMR (CDCl$_3$): 4.39 ppm, t, J=4.5 Hz, 2.0H (OCH$_2$); 4.90 ppm, t, J=4.5 Hz, 2.0H (CH$_2$ONO$_2$); 6.90–7.92 ppm, m, 4.0H (arom. H); 10.42 ppm, s, 1.0H (CH).

EXAMPLE VII 3,5-Dimethoxycarbonyl-2,6-dimethyl-4-[2-(2-nitroxyethoxy)phenyl]-1,4-dihydropyridine A solution of 5 g of the compound from Example VIIb and 7 g of methyl 3-amiocrotonate in methanol was refluxed for 24 hours.

The solution was purified by column chromatography over silica (ethyl acetate/petroleum ether) and crystallized from ethyl acetate/petroleum ether 60-80.

Yield 15%. Empirical formula C$_{19}$H$_{22}$N$_2$O$_8$. Molecular weight 406. Melting point 164°–165° C. TLC system: ether/petroleum ether 60-80: 2/1. R$_f$: 0.22.

NMR data: (CDCl$_3$): 2.27 ppm, s, 6.0H (2×CH$_3$); 3.58 ppm, s, 6.0H (2×OCH$_3$); 4.22–4.43 ppm, m, 2.0H (OCH$_2$); 4.73–4.97 ppm, m, 2.0H (CH$_2$ONO$_2$); 5.24 ppm, s, 1.0H (CH); 5.74 ppm, s, 0.9H (NH); 6.66–7.38 ppm, m, 4.0H (arom. H).

EXAMPLE VIIIa

3-Formylphenoxyacetic Acid

A solution of 3-hydroxybenzaldehyde and 0.3 mol of chloroacetic acid in 300 ml of 2N sodium hydroxide was refluxed for 6 hours. After cooling, the solution was acidified with hydrochloric acid and the precipitate was filtered off and crystallized from ethyl acetate/petroleum ether 60-80.

Yield 40%. Melting point 109°–112° C.

1H-NMR (CDCl$_3$): 4.65 ppm, s, 2.0H (CH$_2$); 7.10–7.60 ppm, m, 4.0H (arom. H); 9.93 ppm, s, 1.0H (CH); 11.0 ppm, bs, 1.0H (OH).

EXAMPLE VIIIb 3-(1,4-Dihydro-3,5-dimethoxycarbonyl-2,6-dimethyl-pyridin-4-yl)phenoxyacetic Acid A solution of 6.0 g of the compound from Example VIIIa and 7.7 g of methyl 3-aminocrotonate in methanol was refluxed for 6 hours and after evaporation of the reaction mixture the residue was dissolved in ethyl acetate. This solution was extracted with aqueous sodium carbonate and after acidification of the aqueous phase a precipitate formed, which was filtered off and dried.

Yield 50%. Melting point 195°–199° C.

EXAMPLE VIII 3,5-Dimethoxycarbonyl-2,6-dimethyl-4-[[3-(2-nitroxyethyl)-aminocarbonyl-methoxy]phenyl]-1,4-dihydropyridine Prepared from 4 g of the compound from Example VIIIb as described in Example III.

Yield 30%. Empirical formula C$_{21}$H$_{25}$N$_3$O$_9$. Molecular weight 463, Melting point 120°–122° C. TLC system: ethyl acetate. R$_f$: 0.73.

NMR data: (CDCl$_3$): 2.30 ppm, s, 6.0H (2×CH$_3$); 3.51–3.80 ppm, m, 8.8H (2×CH$_3$+NCH$_3$); 4.34–4.62 ppm, m, 4.0H (2×OCH$_2$); 4.97 ppm, s, 1.0H (CH); 5.81 ppm, s, 1.0H (NH), 6.50–7.28 ppm, m, 5.0H (arom. H+CONH).

EXAMPLE IXa

4-Formylphenoxyacetic Acid

Prepared from 4-hydroxybenzaldehyde as described in Example VIIIa.

Yield 40%. Melting point 195°–202° C.

1H-NMR (CDCl$_3$-DMSO): 4.66 ppm, s, 2.0H (OCH$_2$); 7.00 ppm, d, J=9.0 Hz, 2.0H (arom. H); 7.80 ppm, d, J=9.0 Hz, 2.0H (arom. H); 9.84 ppm, s, 1.0H (CH); 12.00 ppm, bs, 1.0H (OH).

EXAMPLE IXb

4-[3,5-Dimethoxycarbonyl-2,6-dimethyl-1,4-dihydropyridin-4-yl)phenoxyacetic Acid Prepared from 4 g of the compound from Example IXa as described in Example VIIIb.

Yield 80%. Melting point 195°–199° C.

1H-NMR (DMSO): 2.24 ppm, s, 6.0H (2×CH$_3$); 3.74 ppm, s, 6.0H (2×OCH$_3$); 4.58 ppm, s, 2.0H (OCH$_2$); 4.82 ppm, s, 1.0H (CH); 6.64–7.08 ppm, m, 5.0H (arom. H+NH); 8.86 ppm, s, 1.0H (OH).

EXAMPLE IX 3,5-Dimethoxycarbonyl-2,6-dimethyl-4-[4-[(2-nitroxyethyl)aminocarbonylmethoxy]phenyl-1,4-dihydropyridine Prepared from the compound from Example IXb as described in Example III.

Yield 72%. Empirical formula C$_{21}$H$_{25}$N$_3$O$_9$. Molecular weight 463. Melting point 130°–132° C. TLC system: ethyl acetate. R$_f$: 0.63.

NMR data: (CDCl$_3$): 2.29 ppm, s, 6.0 H (2×CH$_3$); 3.52–3.81 ppm, m, 8.0 H (2×OCH$_3$+NCH$_3$); 4.39 ppm, s, 2.0 H (OCH$_2$C); 4.49 ppm, t, J=5.1 Hz, 2.0 H (CH$_2$O-NO$_2$); 4.93 ppm, s, 0.9 H (CH); 5.90 ppm, s, 1.0 H (NH); 6.60–7.30 ppm, m, 5.2 H (arom. H+CONH).

EXAMPLE Xa

4-Formyl-2-methoxyphenoxyacetic acid

Prepared from 4-hydroxy-3-methoxybenzaldehyde as described in Example VIIIa.

Yield 57%.

1H-NMR (DMSO): 3.88 ppm, s, 3.0 H (OCH$_3$); 4.84 ppm, s, 2.0 H (OCH$_2$); 7.06 ppm, d, J=7.6 Hz, 1.0 H (arom. H); 7.38–7.64 ppm, m, 2.0 H (arom. H); 9.82 ppm, s, 1.0 H (CH); 12.00 ppm, bs, 1.0 H (OH).

EXAMPLE Xb 4-(3,5-Dimethoxycarbonyl-2,6-dimethyl-1,4-dihydropyridin-4-yl)-3-methoxyphenoxyacetic acid Prepared from the compound from Example Xa as described in Example VIIIb.

Yield 30%. Melting point 172°–176° C.

1H-NMR (DMSO); 2.27 ppm, s, 6.0 H (2×CH$_3$); 3.58 ppm, s, 6.0 H (2×OCH$_3$); 3.72 ppm, s, 3.0 H (OCH$_3$); 4.58 ppm, s, 2.0 H (OCH$_2$); 4.83 ppm, s, 1.0 H (CH); 6.57–6.80 ppm, m, 4.0 H (arom. H+NH); 8.84 ppm, s, 1.0 H (OH).

EXAMPLE X 3,5-Dimethoxycarbonyl-2,6-dimethyl-4-[3-methoxy-4-[(2-nitroxyethyl)aminocarbonylmethoxy]phenyl]-1,4-dihydropyridine Prepared from the compound from Example Xb as described in Example III.

Empirical formula C$_{22}$H$_{27}$N$_3$O$_{10}$. Molecular weight 493. Melting point 149°–150° C. TLC system: ethyl acetate. R$_f$: 0.63.

NMR data: (CDCl$_3$):2.31 ppm, s, 6.0 H (2×CH$_3$); 3.56–3.92 ppm, m, 11.0 H (3×OCH$_3$+NCH$_2$); 4.40–4.65 ppm, m, 4.0 H (2×OCH$_2$); 4.86 ppm, s, 1.0 H (CH); 6.00 ppm, s, 0.9 H (NH); 6.68–6.96 ppm, m, 3.0 H (arom. H); 7.50 ppm, bs, 1.0 H (CONH).

EXAMPLE XIa

2-Ethoxy-6-formylphenoxyacetic acid

Prepared as described in Example VIIIa from 3-ethoxy-2-hydroxybenzaldehyde. Crystallized from ethyl acetate/petroleum ether 60–80.

Yield 40%. Melting point 105°–108° C.

1H-NMR (CDCl$_3$): 1.50 ppm, t, J=6.3 Hz, 3.0 H (CH$_3$); 4.11 ppm, q, J=6.9 Hz, 2.0 H (OCH$_2$); 4.82 ppm, s, 2.0 H (OCH$_2$); 7.11–7.28 ppm, m, 3.0 H (arom. H); 8.04 ppm, bs, 1.5 H (OH+H$_2$O); 10.14 ppm, s, 1.0 H (CH).

EXAMPLE XIb

3-Ethoxy-6-(3,5-dimethoxycarbonyl-2,6-dimethyl-1,4-dihydropyridin-4-yl)phenoxyacetic acid Prepared in accordance with Example XIa as described in Example VIIIb.

Crystallized from ethyl acetate/petroleum ether 60–80. Yield 42%. Melting point 205°–211° C.

1H-NMR (CDCl$_3$-DMSO): 1.21 ppm, t, J=7.1 Hz, 3.0 H (CCH$_3$); 2.27 ppm, s, 5.8 H (2×CH$_3$); 3.58 ppm, s, 6.0 H (2×OCH$_3$); 3.97 ppm, q, J=7.1 Hz, 2.0 H (CH$_2$); 4.54 ppm, s, 2.0 H (OCH$_2$); 5.23 ppm, s, 0.9 H (CH); 6.60–6.96 ppm, m, 3.1 H (arom. H); 8.14 ppm, s, 1.0 H (NH); 12.00 ppm, bs, 1.0 H (CH).

EXAMPLE XI 3,5-Dimethoxycarbonyl-2,6-dimethyl-4-[3-ethoxy-2-[(2-nitroxyethyl)aminocarbonylmethoxy]phenyl]-1,4-dihydropyridine Prepared from the compound from Example XIb as described in Example III.

Yield 70%. Empirical formula $C_{23}H_{29}N_3O_{10}$. Molecular weight 507. Melting point 159°–160° C. TLC system: diethyl ether. $R_f$ 0.69.

NMR data: (CDCl$_3$): 1.42 ppm, t, J=7.2 Hz; 3.0 H (CH$_3$); 2.32 ppm, s, 6.0 H (2×CH$_3$); 3.56–4.18 ppm, m, 10.0 H (2×OCH$_3$+NCH$_3$+OCH$_2$); 4.52–4.70 ppm, m, 4.0 H (OCH$_2$CO+CH$_2$ONO$_2$); 5.21 ppm, s, 1.0 H (CH); 5.83 ppm, s, 0.9 H (NH); 6.57–7.00 ppm, m, 3.0 H (arom. H); 8.88 ppm, bs, 1.0 H (NH).

EXAMPLE XIIa

4-Bromo-6-formylphenoxyacetic acid

Prepared from 3-bromo-6-hydroxybenzaldehyde as described in Example VIIIa. Recrystallized from ethyl acetate/petroleum ether 60–80.

Yield 35%. Melting point 159°–164° C.

1H-NMR (CDCl$_3$-DMSO): 5.75 ppm, s, 2.0 H (CH$_2$); 6.90 ppm, d, J=9.0 Hz; 1.0 H (arom. H); 7.54–7.72 ppm, m, 1.0 H (arom. H); 7.85 ppm, d, J=2.7 Hz, 1.0 H (arom. H); 9.80 ppm, bs, 1.0 H (OH); 10.40 ppm, s, 1.0 H (CH).

EXAMPLE XIIb

4-Bromo-6-(3,5-dimethoxycarbonyl-2,6-dimethyl-1,4-dihydropyridin-4-yl)phenoxyacetic acid Prepared from the compound from Example XIIa as described in Example VIIIb.

Yield 32%. Melting point 219°–222° C.

1H-NMR (DMSO): 2.30 ppm, s, 5.7 H (2×CH$_3$); 3.60 ppm, s, 6.0 H (2×OCH$_3$); 4.70 ppm, s, 2.0 H (OCH$_2$); 5.27 ppm, s, 1.0 H (CH); 6.80 ppm, d, J=8.7 Hz, 1.0 H (arom. H); 7.12–7.40 ppm, m, 2.0 H (arom. H); 8.84 ppm, s, 1.0 H (NH); 9.00 ppm, bs, 1.0 H (OH).

EXAMPLE XII

4-(5-Bromo-2-[(2-nitroxyethyl)aminocarbonylmethoxy]-phenyl]-3,5-dimethoxycarbonyl-2,6-dimethyl-1,4-dihydropyridine Prepared from the compound from Example XIIb as described in Example III.

Empirical formula $C_{21}H_{24}BrN_3O_9$. Molecular weight 542. Melting point 166°–167° C. TLC system: diethyl ether. $R_f$ 0.38.

NMR data: (CDCl$_3$): 2.32 ppm, s, 6.0 H (2×CH$_3$); 3.50–3.80 ppm, m, 8.0 H (NCH$_2$+2×OCH$_3$); 4.46–4.68 ppm, m, 4.0 H (2×OCH$_2$); 5.42 ppm, s, 1.0 H (CH); 5.84 ppm, s, 1.0 H (NH); 6.56 ppm, d, J=8.5 Hz, 1.0 H (arom. H); 7.08–7.35 ppm, m, 2.0 H (arom. H); 8.54 ppm, bs, 1.0 H (CONH).

EXAMPLE XIIIa

2-Formylphenoxy-N-hydroxyethylacetamide

Prepared from 2-formylphenoxyacetic acid as described in Example III.

Yield 60%. Melting point 116°–121° C.

1H-NMR (CDCl$_3$): 3.19 ppm, bs, 1.0 H (OH); 3.42–3.92 ppm, m, 4.0 H (CH$_2$—CH$_2$); 4.60 ppm, s, 2.0 H (OCH$_2$); 6.82–8.20 ppm, m, 5.1 H (arom. H+NH); 10.80 ppm, s, 0.9 H (CH)

EXAMPLE XIIIb

2-(2-Formyl-4-nitrophenoxy)-N-nitroxyethylacetamide 2.9 g of the compound from Example XIIIa were added slowly to 25 ml of nitric acid while the temperature was kept between 0° and 5° C. After everything had bee added, the solution was poured into ice-water. The precipitate was filtered off, washed with water and dried.

Yield 76%. Melting point 113°–116° C.

1H-NMR (CDCl$_3$-DMSO): 3.84 ppm, q, J=5.4 Hz, 2.0 H (NCH$_2$); 4.60 ppm, t, J=5.4 Hz, 2.0 H (CH$_2$O-NO$_2$); 4.77 ppm, s, 2.0 H (CH$_2$O); 7.11 ppm, d, J=9.0 Hz, 1.0 H (arom. H); 8.20–8.56 ppm, m, 1.8 H (arom. H+NH); 8.67 ppm, d, J=2.7 Hz, 1.0 H (arom. H); 10.40 ppm, s, 1.0 H (CH).

EXAMPLE XIII

3,5-Dimethoxycarbonyl-2,6-dimethyl-4-[5-nitro-2-[(2-nitroxyethyl)aminocarbonylmethoxy]phenyl]-1,4-dihydropyridine A solution of 3 g of the compound from Example XIIIb and 2.2 g of methyl 3-aminocrotonate in methanol was refluxed for five hours. After concentrating the reaction mixture under reduced pressure and cooling in ice, the compound crystallized.

Yield 22%. Empirical formula $C_{21}H_{24}N_4O_{11}$. Molecular weight 508. Melting point 189°–192° C. TLC system: ethyl acetate. $R_f$ 0.64.

NMR data (DMSO): 2.35 ppm, s, 5.8 H (2×CH$_3$); 3.38–3.70 ppm, m, 8.0 H (2×OCH$_3$+NCH$_2$); 4.58 ppm, t, J=5.2 Hz, 2.0 H (CH$_2$ONO$_2$); 4.73 ppm, s, 2.0 H (OCH$_2$); 5.32 ppm, s, 1.0 H (CH); 7.0 ppm, d, J−9.9 Hz, 1.0 H (arom. H); 7.88–8.07 ppm, m, 2.0 H (arom. H); 8.23 ppm, bs, 1.0 H (CONH); 8.93 ppm, s, 0.9 H (NH).

EXAMPLE XIVa

2-(2-Nitroxyethoxy)-5-nitrobenzaldehyde 5 g of the compound from Example VIIa were added to nitric acid while the temperature was kept below −5° C. After everything had been added, the mixture was stirred for a further 5 minutes and then poured into ice-water. After extraction with ethyl acetate, the organic layer was washed with dilute sodium carbonate solution, dried over MgSO$_4$ and evaporated. The residue was crystallized from ethyl acetate/petroleum ether 60–80.

Yield 80%.

1H-NMR (CDCl$_3$): 4.53, ppm,, t, J=4.5 Hz, 2.0 H (phenyl-OCH$_2$); 4.94 ppm, t, J=4.5 Hz, 2.0 H (CH$_2$O-NO$_2$); 7.12 ppm, d, J=9.4 Hz, 1.0 H (arom. H); 8.42 ppm, double doublet, J1=9.4 Hz, J2=3.1 Hz, 1.0 H (arom. H); 9.65 ppm, d, J=3.1 Hz, 0.9 H (arom. H); 10.44 ppm, s, 0.9 H (CH).

EXAMPLE XIV

3,5-Dimethoxycarbonyl-2,6-dimethyl-4-[2-(2-nitroxyethoxy)-5-nitrophenyl]-1,4-dihydropyridine A solution of 4 g of the compound from Example XIVa and 4 g of methyl 3-aminocrotonate in methanol was refluxed for 30 hours. The compound was purified by chromatography (silica, ethyl acetate:petroleum ether 60–80/1:1) and crystallized from methanol.

Yield 21%. Empirical formula $C_{19}H_{21}N_3O_{10}$. Molecular weight 451. Melting point 214°–215° C. TLC system: diethyl ether. $R_f$ 0.80.

NMR data (CDCl$_3$): 1.63 ppm, s, 2.0 H (H$_2$O); 2.33 ppm, s, 5.9 H (2×CH$_3$); 3.58 ppm, s, 6.2 H (2×OCH$_3$); 4.25–4.45 ppm, m, 2.0 H (phenyl-OCH$_2$); 4.77–4.97 ppm, m, 2.0 H (CH$_2$ONO$_2$); 5.32 ppm, s, 1.0 H (CH); 5.75 ppm, bs, 1.0 H (NH); 6.80 ppm, d, J=9.0 Hz, 1.0 H (arom. H); 7.92–8.21 ppm, m, 2.0 H (arom. H).

EXAMPLE XVa

3-Chloro-6-(2-hydroxyethoxy)benzaldehyde

Prepared from 25 g of 3-chloro-6-hydroxybenzaldehyde, 14 g of ethylene carbonate and 45 g of tetraethylammonium bromide as described in Example VIIa. The compound was purified by chromatography (silica, ethyl acetate:petroleum ether 60–80/2:1).

Yield 60%. Melting point 65°–68° C.

H-NMR (CDCl$_3$): 2.87 ppm, bs, 0.8 H (OH); 3.90–4.32 ppm, m, 4.0 H (CH$_2$CH$_2$); 6.84–7.84 ppm, m, 3.0 H (arom. H); 10.34 ppm, s, 1.0 H (CH).

EXAMPLE XVb 3-chloro-6-(3-nitroxyethoxy)benzaldehyde

Prepared from 8 g of the compound from Example XVa, 5 ml of nitric acid and 12.5 ml of acetic anhydride as described in Example IIb. The compound was purified by chromatography (silica, CH$_2$Cl$_2$).

Yield 60%.

H-NMR (CDCl$_3$): 4.34 ppm, t, J=4.5 Hz, 1.9 H (phenyl-OCH$_2$); 4.90 ppm, t, J=4.5 Hz, 1.9 H (CH$_2$ONO$_2$); 6.80–7.87 ppm, m, 3.0 H (arom. H); 10.34 ppm, s, 0.9 H (CH).

EXAMPLE XV

4-[3-Chloro-6-(2-nitroxyethoxy)phenyl]-3,5-dimethoxycarbonyl-2,6-dimethyl-1,4-dihydropyridine A solution of 8.5 g of the compound from Example XVb and 8 g of methyl 3-aminocrotonate in 200 ml of methanol was refluxed for 50 hours. The compound was purified by chromatography (silica, ethyl acetate: petroleum ether 60–80/1:2).

Crystallized from ethyl acetate/petroleum ether 60–80. Yield 15%.

The ethylacetate of the compound formed under the above conditions melted between 60° and 70° C., solidified again and the pure compound melted again at 150°–152° C.

Empirical formula C$_{23}$H$_{29}$ClN$_2$O$_{10}$. Molecular weight 528.5. Melting point 150°–152° C. TLC system: ethyl acetate:petroleum ether 60–80/1:1. R$_f$: 0.55.

NMR data: (CDCl$_3$): 1.26 ppm, t, J=7.2 Hz, 3.0 H (CH$_3$-ethyl acetate); 2.05 ppm, s, 3.0 H (CH$_3$-ethyl acetate); 2.29 ppm, s, 6.0 H (2×CH$_3$); 3.60 ppm, s, 6.1 H (2×OCH$_3$); 4.00–4.32 ppm, m, 4.1 H (phenyl-OCH$_2$+CH$_2$-ethyl acetate); 4.74–4.93 ppm, m, 2.0 H (CH$_2$ONO$_2$); 5.20 ppm, s, 1.0 H (CH); 5.73 ppm, bs, 0.9 H (NH); 6.58–7.23 ppm, m, 3.0 H (arom. H).

EXAMPLE XVI 3,5-Diethoxycarbonyl-2,6-dimethyl-4-[4-(2-nitroxyethoxy)phenyl]-1,4-dihydropyridine A solution of 5 g of 4-(2-nitroxyethoxy)benzaldehyde and 6.1 g of ethyl 3-aminocrotonate in 100 ml of ethanol was refluxed for 20 hours.

The compound was purified by chromatography (silica, CH$_2$Cl$_2$). Crystallized from diethyl ether/petroleum ether 60–80.

Yield 45%. Empirical formula C$_{21}$H$_{26}$N$_2$O$_8$. Molecular weight 434. Melting point 122°–125° C. TLC system: ethyl acetate:petroleum ether 60–80/1:1. R$_f$: 0.34.

NMR data: (CDCl$_3$): 1.21 ppm, t, J=7.2 Hz, 6.0 H (2×ethyl-CH$_3$); 2.28 ppm, s, 6.0 H (2×CH$_3$); 3.92–4.26 ppm, m, 6.2 H (phenyl OCH$_2$+2×ethyl-CH$_2$); 4.66–4.86 ppm, m, 2.0 H (CH$_2$ONO$_2$); 4.93 ppm, s, 1.0 H (CH); 5.66 ppm, bs, 1.1 H (NH); 6.72 ppm, d, J=8.6 Hz, 2.0 H (arom. H); 7.20 ppm, d, J=8.6 Hz, 2.0 H (arom. H).

EXAMPLE XVIIa 2-(2-Hydroxyethoxy)-3-methoxybenzaldehyde

Prepared as described in Example VIIa.

Yield 70%. Boiling point 140° C. (0.1 mm Hg).

1H-NMR (CDCl$_3$): 3.21 ppm, t, J=5.8 Hz, 0.9 H (OH); 3.79–4.38 ppm, m, 7.0 H (CH$_2$CH$_2$CH$_3$); 7.0–7.58 ppm, m, 3.0 H (arom. H); 10.34 ppm, 0.9 H (CH).

EXAMPLE XVIIb

3-Methoxy-2-(2-nitroxyethoxy)benzaldehyde

Prepared as described in Example VIIb. Purified by chromatography (silica, ethyl acetate:petroleum ether 60–80/2:3). Crystallized from ethyl acetate/petroleum ether 60–80.

Yield 50%. Melting point 70–°71° C.

1H-NMR (CDCl$_3$): 3.90 ppm, s, 3.0 H (CH$_3$); 4.37–4.56 ppm, m, 2.0 H (OCH$_2$); 4.74–4.95 ppm, m, 2.0 H (CH$_2$ONO$_2$); 7.14–7.56 ppm, m, 3.0 H (arom. H); 10.44 ppm, s, 1.0 H.

EXAMPLE XVII 3,5-Dimethoxycarbonyl-2,6-dimethyl-4-[3-methoxy-2-(2-nitroxyethoxy)phenyl]-1,4-dihydropyridine×H$_2$O Prepared as described in Example VII.

Purified by chromatography (silica, ethyl acetate:petroleum ether 60–80/1:2). Crystallized from ethyl acetate/petroleum ether 60–80.

Yield 30%. Empirical formula C$_{20}$H$_{24}$N$_2$O$_9$. Molecular weight 454. Melting point 122°–123° C. TLC system: ethyl acetate:petroleum ether 60–80/1:1. R$_f$: 0.62.

NMR data (CDCl$_3$): 1.91 ppm, s, 1.9 H (H$_2$O); 2.28 ppm, s, 6.0 H (2×CH$_3$); 3.61 ppm, s, 6.0 H (2×ester-CH$_3$); 3.82 ppm, s, 3.0 H (ether-CH$_3$); 4.21–4.38 ppm, m, 2.0 H (phenyl-OCH$_2$); 4.81–5.00 ppm, m, 2.0 H (CH$_2$ONO$_2$); 5.31 ppm, s, 1.0 H (CH); 6.07 ppm, bs, 0.9 H (NH); 6.66–7.10 ppm, m, 3.0 H (arom. H).

EXAMPLE XVIIIa

3-Ethoxy-2-(hydroxyethoxy)benzaldehyde

A mixture of 40 g of 3-ethoxysalicylaldehyde, 22 g of ethylene carbonate and 40 g of tetraethylammonium bromide was heated at 140° C. for 4 hours. After cooling to room temperature ethyl acetate was added to the reaction mixture, the solid material was filtered off, the filtrate was washed with water and the organic phase was dried over magnesium sulfate and evaporated. The residue was distilled under reduced pressure.

Yield 70%. Boiling point 140°–145° C. (0.1 mm Hg).

1H-NMR (CDCl$_3$): 1.50 ppm, t, J=7.0 Hz, 3.0 H (CH$_3$); 3.77–4.40 ppm, m, 7.0 H (3×CH$_2$, OH); 6.90–7.53 ppm, m, 3.0 H (arom. H); 10.32 ppm, s, 0.9 H (CH).

EXAMPLE XVIIIb

3-Ethoxy-2-(2-nitroxyethoxy)benzaldehyde

A mixture of 2 ml of nitric acid and 5 ml of acetic anhydride was added at 0° C. to a solution of 5 g of the compound from Example XVIIIa in ethyl acetate. After stirring for 5 minutes, 100 ml of water were added to the reaction mixture and the remaining mixture was stirred for a further 30 minutes. The organic phase was washed with aqueous sodium carbonate, dried over magnesium sulfate and evaporated.

Yield 70%.

1H-NMR (CDCl$_3$): 1.46 ppm, t, J=7.0 Hz, 3.0 H (CH$_3$); 4.13 ppm, q, J=7.0 Hz, 2.0 H (ethyl-CH$_2$); 4.38–4.63 ppm, m, 2.0 H (CH$_2$CONO$_2$); 4.82–5.00 ppm, m, 2.0 H (CH$_2$ONO$_2$); 7.04–7.54 ppm, m, 3.0 H (arom. H); 10.44 ppm, s, 0.9 H (CH).

EXAMPLE XVIII 3,5-Dimethoxycarbonyl-2,6-dimethyl-4-[3-ethoxy-2-(2-nitroxyethoxy)phenyl]-1,4-dihydropyridine×H$_2$O A solution of 4.5 g of 3-ethoxy-2-nitroxyethoxybenzaldehyde and 4.7 g of methyl 3-aminocrotonate in 100 ml of methanol was refluxed for 140 hours. The compound was purified by chromatography (silica; ethyl acetate:petroleum ether 60–80/1:1) and crystallized from ethyl acetate/petroleum ether 60–80.

Yield 20%. Empirical formula C$_{21}$H$_{28}$N$_2$O$_{10}$. Molecular weight 468. Melting point 108°–110° C. TLC system ethyl acetate:petroleum ether 60–80/1:1. R$_f$ 0.68.

NMR data: (CDCl$_3$): 1.43 ppm, t, J=7.2 Hz, 3.0 H (ether CH$_3$); 1.60 ppm, s, 1.8 H (H$_2$O); 2.29 ppm, s, 6.0 H (2×CH$_3$); 3.62 ppm, s, 6.0 H (2×OCH$_3$); 4.04 ppm, q, J=7.2 Hz, 2.0 H (ethyl CH$_2$); 4.17–4.37 ppm, m, 2.0 H (CH$_2$CONO$_2$); 4.81–4.98 ppm, m, 2.0 H (CH$_2$ONO$_2$); 5.26 ppm, s, 1.0 H (CH); 5.69 ppm, bs, 0.9 H (NH); 6.62–6.96 ppm, m, 3.0 H (arom. H).

EXAMPLE XIXa

5-Bromo-2-(2-hydroxyethoxy)benzaldehyde

Prepared as described in Example VIIa. Purified by chromatography (silica; ethyl acetate).

Yield 60%. Melting point 70–°74° C.

1H-NMR (CDCl$_3$): 2.45 ppm, bs, 1.1 H (OH); 3.96–4.34 ppm, m, 4.0 H (CH$_2$CH$_2$); 6.93 ppm, d, J=8.8 Hz, 1.0 H (arom. H); 7.65 ppm, double doublet, J1=8.8 Hz, J2=2.5 Hz, 1.0 H (arom. H); 7.92 ppm, d, J=2.5 Hz, 1.0 H (arom. H); 10.40 ppm, s, 0.8 H (CHO).

EXAMPLE XIXb

5-Bromo-2-(2-nitroxyethoxy)benzaldehyde

Prepared as described in Example VIIb. Purified by chromatography (silica; ethyl acetate:petroleum ether 60–80/1:2).

Yield 43%.

1H-NMR (CDCl$_3$): 4.31–4.52 ppm, m, 2.0 H (CH$_2$CONO$_2$); 4.82–5.05 ppm, m, 2.0 H (CH$_2$ONO$_2$); 6.92 ppm, d, J=9.0 Hz, 1.0 H (arom. H); 7.97 ppm, double doublet, J1=9.0 Hz, J2=2.5 Hz, 1.0 H (arom. H); 7.97 ppm, d, J=2.5 Hz, 1.0 H (arom. H); 10.40 ppm, s, 1.0 H (CHO).

EXAMPLE XIX

4-[5-Bromo-2-(2-nitroxyethoxy)phenyl]-3,5-dimethoxycarbonyl-2,6-dimethyl-1,4-dihydropyridine Prepared as described in Example XVIII. Purified by chromatography (silica; ethyl acetate:petroleum ether 60–80/1:2).

Yield 20%. Empirical formula C$_{19}$H$_{21}$BrN$_2$O$_8$. Molecular weight 485. Melting point 157°–159° C. TLC system: ethyl acetate:petroleum ether 60–80/1:1. R$_f$ 0.62.

NMR data: (CDCl$_3$): 2.31 ppm, s, 6.0 H (2×CH$_3$); 3.63 ppm, s, 6.0 H (2×OCH$_3$); 4.14–4.33 ppm, m, 2.0 H (CH$_2$CONO$_2$); 4.76–4.96 ppm, m, 2.0 H (CH$_2$ONO$_2$); 5.24 ppm, s, 1.0 H (CH); 5.65 ppm, bs, 0.9 H (NH); 6.64 ppm, d, J=8.8 Hz, 1.0 H (arom. H); 7.14–7.42 ppm, m, 2.0 H (arom. H).

EXAMPLE XXa

2-{2-[2-(2-Hydroxyethoxy)ethoxy]ethoxy}benzaldehyde

A solution of 10 g of sodium salt of salicylaldehyde and 10 g of 2-[2-(2-chloroethoxy)ethoxy]ethanol in dimethylformamide was refluxed for 50 hours. After evaporation, the residue was dissolved in ethyl acetate and the solution washed with water, dried over magnesium sulfate and evaporated. The compound was purified by chromatography (silica; ethyl acetate).

Yield 34%, oil.

1H-NMR (CDCl$_3$): 3.00 ppm, bs, 1.1 H (OH); 3.30–4.40 ppm, m, 12.5 H (6×CH$_2$); 6.80–8.00 ppm, m, 4.0 H (arom. H); 10.58 ppm, s, 1.0 H (CHO).

EXAMPLE XXb

2-{2-[2-(2-Nitroxyethoxy)ethoxy]ethoxy}benzaldehyde

Prepared as described in Example VIIb. Purified by chromatography (silica; ethyl acetate:petroleum ether 60–80/1:1).

Yield 76%, oil.

1H-NMR (CDCl$_3$): 3.58–4.04 ppm, m, 8.0 H (CH$_2$—O—CH$_2$CH$_2$—O—CH$_2$): 4.18–4.40 ppm, m, 2.0 H (phenyl-OCH$_2$); 4.54–4.76 ppm, m, 2.0 H (CH$_2$O-NO$_2$); 6.92–7.99 ppm, m, 4.0 H (arom. H); 10.52 ppm, s, 0.9 H (CHO).

EXAMPLE XX 3,5-Diethoxycarbonyl-2,6-dimethyl-4-(2-{2-[2-(2-nitroxy-ethoxy)ethoxy]ethoxy}-phenyl)-1,4-dihydropyridine Prepared as described in Example VII. Purified by chromatography (silica; ethyl acetate:petroleum ether 60–80/1:1).

Yield 20%. Empirical formula C$_{25}$H$_{34}$N$_2$O$_{10}$. Molecular weight 522. Melting point 93°–95° C. TLC system: ethyl acetate:petroleum ether 60–80/2:1. R$_f$ 0.52.

NMR data: (CDCl$_3$): 1.19 ppm, t, J=7.0 Hz, 6.0 H (2×OCCH$_3$); 2.24 ppm, s, 6.0 H (2×CH$_3$); 3.35–4.22 ppm, m, 14.0 H (phenyl—O—(CH$_2$CH$_2$)$_2$—O—CH$_2$, 2×ester-CH$_2$); 4.56–4.76 ppm, m, 2.0 H (CH$_2$ONO$_2$); 5.10 ppm, s, 1.0 H (CH); 6.54 ppm, bs, 0.9 H (NH); 6.74–7.40 ppm, m, 4.0 H (arom. H).

EXAMPLE XXI

3,5-Diethoxycarbonyl-2,6-dimethyl-4-[2-(2-nitroxyethoxy)phenyl]-1,4-dihydropyridine A solution of 5 g of compound from Example VIIb and 6.1 g of ethyl 3-aminocrotonate in ethanol was refluxed for 44 hours. The compound was purified by chromatography (silica; ethyl acetate:petroleum ether 60–80/1:2) and crystallized from ethyl acetate/petroleum ether 60–80.

Yield 24%. Empirical formula $C_{21}H_{26}N_2O_8$. Molecular weight 434. Melting point 138°–139° C. TLC system: ethyl acetate:petroleum ether 60–80/1:1. $R_f$: 0.64.

NMR data: (CDCl$_3$): 1.16 ppm, t, J=7.2 Hz, 6.0 H (2×ester-CH$_3$); 2.29 ppm, s, 6.0 H (2×CH$_3$); 4.02 ppm, q, J=7.2 Hz, 4.0 H (2×ester-CH$_2$); 4.14–4.32 ppm, m, 2.0 H (CH$_2$CON); 4.73–4.90 ppm, m, 2.0 H (CH$_2$ON); 5.21 ppm, s, 1.0 H (CH); 5.60 ppm, bs, 1.0 H (NH); 6.68–7.40 ppm, m, 4.0 H (arom. H).

EXAMPLE XXIIa

2-(2,2-Dimethyl-3-hydroxypropoxy)benzaldehyde

A solution of 20 g of salicylaldehyde, 30 g of 3-bromo-2,2-dimethylpropanol and 22 g of potassium carbonate in DMF was refluxed for 24 hours. After evaporation, the residue was dissolved in ethyl acetate and the solution was washed with water. The organic phase was dried over magnesium sulfate and evaporated. The residue was purified by chromatography (silica; dichloromethane).

Yield 25%.

1H-NMR (CDCl$_3$): 1.06 ppm, s, 6.0 H (2×CH$_3$); 2.60 ppm, bs, 1.0 H (OH); 3.60 ppm, s, 2.0 H (hydroxyl-CH$_2$); 3.90 ppm, s, 2.0 H (phenoxy-CH$_2$); 6.90–7.90 ppm, m, 4.0 H (arom. H); 10.40 ppm, s, 1.0 H (CHO).

EXAMPLE XXIIb

2-(2,2-Dimethyl-3-nitroxypropoxy)benzaldehyde

Prepared from the compound from Example XXIIa as described in Example VIIb. Purified by chromatography (silica; dichloromethane).

Yield 82%.

1H-NMR (CDCl$_3$): 1.20 ppm, s, 6.0 H (2×CH$_3$), 3.90 ppm, s, 2.0 H (phenoxy-CH$_2$), 4.46 ppm, s, 2.0 H (CH$_2$ON); 6.88–7.98 ppm, m, 4.0 H (arom. H); 10.50 ppm, s, 1.0 H (CHO).

EXAMPLE XXII

3,5-Diethoxycarbonyl-2,6-dimethyl-4-[2-(2,2-dimethyl-3-nitroxypropoxy)-phenyl]-1,4-dihydropyridine Prepared from the compound from Example XXIIb and ethyl 3-aminocrotonate as described in Example VII. Purified by chromatography (silica; ethyl acetate: petroleum ether 60–80/1:4). The residue, obtained after evaporation of the fractions containing the pure compound, was treated with petroleum ether 40–80, whereupon it solidified.

Yield 20%. Empirical formula $C_{24}H_{32}N_2O_8$. Molecular weight 476. Melting point 97°–98° C. TLC system: ethyl acetate:petroleum ether 60–80/2:5. $R_f$: 0.35.

NMR data: (CDCl$_3$): 0.97–1.32 ppm, m, 12.0 H (2×OCCH$_3$,CC(CH$_3$)$_2$C); 2.23 ppm, s, 6.0 H (2×CH$_3$); 3.78 ppm, s, 2.0 H (phenoxy-OCH$_2$); 3.87–4.27 ppm, m, 4.0 H (2×ester-CH$_2$); 3.64 ppm, s, 2.0 H (CH$_2$ON); 5.36–5.56 ppm, m, 2.0 H (CH,NH); 6.60–7.38 ppm, m, 4.0 H (arom. H).

EXAMPLE XXIIIa

α-Acetyl-β-[2-(2,2-methyl-3-nitroxypropoxy)phenyl]acrylate

A solution of 6,5 g of the compound from Example XXIIb, 3 g of methyl acetoacetate, 0.2 ml of piperidine and 0.6 ml of acetic acid was heated for 3 hours in a Dean Stark apparatus. The solution was washed successively with dilute hydrochloric acid and aqueous sodium carbonate, dried over magnesium sulfate and evaporated. The residue was purified by chromatography (silica; petroleum ether 60–80:ethyl acetate/4:1).

Yield 90%.

1H-NMR (CDCl$_3$, cis isomer): 1.18 ppm, s, 6.0 H (CC(CH$_3$)$_2$C); 2.30 ppm, s, 3.0 H (CH$_3$CO); 3.79–3.93 ppm, m, 5.0 H (phenoxy-CH$_2$OCH$_3$); 4.47 ppm, s, 2.0 H (CH$_2$ON); 6.83–7.10 ppm, m, 2.0 H (arom. H); 7.24–7.54 ppm, m, 2.0 H (arom. H); 8.10 ppm, s, 1.0 H (CH).

1H-NMR (CDCl$_3$, trans isomer): 1.18 ppm, s, 6.0 H (CC(CH$_3$)$_2$C); 2.26 ppm, s, 3.0 H (CH$_3$CO); 3.73–3.93 ppm, m, 5.0 H (phenoxy CH$_2$, OCH$_3$); 4.46 ppm, s, 2.0 H (CH$_2$ON); 6.80–7.11 ppm, m, 2.0 H (arom. H); 7.26–7.54 ppm, m, 2.0 H (arom. H); 8.00 ppm, s, 1.0 H (CH).

EXAMPLE XXIII

2,6-Dimethyl-4-[2-(2,2-dimethyl-3-nitroxypropoxy)-phenyl]-3-ethoxycarbonyl-5-methoxycarbonyl-1,4-dihydro-pyridine×H$_2$O A solution of 6 g of the compound from Example XXIIIa and 2.2 g of ethyl 3-aminocrotonate was refluxed for 18 hours in propan-2-ol. The title compound was purified by chromatography (silica; ethyl acetate: petroleum ether 60–80/1:40) and crystallized from methanol/water.

Yield 59%. Empirical formula $C_{23}H_{32}N_2O_9$. Molecular weight 480. Melting point 55°–56° C. TLC system: ethyl acetate: petroleum ether 60–80/2:5. $R_f$: 0.35.

NMR data: (CDCl$_3$): 100–1.30 ppm, m, 9.0 H (CC(CH$_3$)$_2$C, OCCH$_3$); 2.25 ppm, d, J=1.5 Hz, 6.0 H (2×CH$_3$); 3.56 ppm, s, 3.0 H (ester-CH$_3$); 3.79 ppm, s, 2.0 H (phenoxy-CH$_2$); 3.86–4.25 ppm, m, 2.0 H (ester-CH$_2$); 3.66 ppm, d, J=2.3 Hz, 2.0 H (CH$_2$ON); 5.43 ppm, 5, 1.0 H (CH); 5.70 ppm, bs, 1.0 H (NH); 6.68–7.40 ppm, m, 4.0 H (arom. H).

EXAMPLE XXIVa

4-Bromomethyl-(trans)-cyclohexylmethanol

A solution of 60 g of 1,4-(trans)-cyclohexyldimethanol in 300 ml of 48% hydrobromic acid was heated at 90° C. for 20 hours while this solution was extracted continuously with petroleum ether 100–140. After cooling the reaction mixture, the petroleum ether 100–140 was evaporated and the residue was purified by distillation under reduced pressure.

Yield 50%.

Boiling point 150° C. (10 mm Hg).

1H-NMR (CDCl$_3$): 0.72–2.26 ppm, m, 10.0 H (cyclohexyl-H); 3.25–3.58 ppm, m, 5.0 H (BrCH$_2$, CH$_2$OH).

EXAMPLE XXIVb

2-[(4-Hydroxymethyl-(trans)-cyclohexyl)methoxy]benzaldehyde

A mixture of 13 g of salicylaldehyde, 20 g of the compound from Example XXIVa and 5.8 g of potassium hydroxide in 100 ml of dimethyl sulfoxide was stirred for 4 hours while heating at 130° C. After cooling to room temperature, the mixture was diluted with water and the resulting mixture was extracted with diethyl ether. After evaporation of the ether, the residue was purified by chromatography (silica; ethyl acetate:petroleum ether 60-80/1:2).

Yield 38%.

1H-NMR (CDCl$_3$): 0.85-2.11 ppm, m, 11.0 H (cyclohexyl H, OH); 3.50 ppm, d, J=5.6 Hz, 2.0 H (hydroxy-CH$_2$); 3.92 ppm, d, J=5.6 Hz, 2.0 H (phenoxy-CH$_2$); 6.87-7.92 ppm, m, 4.0 H (arom. H); 10.53 ppm, s, 1.0 H (CH).

EXAMPLE XXIVc

2-[(4-Nitroxymethyl-(trans)-cyclohexyl)methoxy]benzaldehyde

A mixture of 11.1 ml of acetic anhydride and 4.6 ml of nitric acid was added at 0° C. to a solution of 8.0 g of the compound from Example XXIVb in ethyl acetate. After everything had been added, the mixture was stirred for a further 15 minutes and then poured into water. This mixture was stirred for 1 hour and then extracted with ethyl acetate. After drying and evaporation of the ethyl acetate, the residue was purified by chromatography (silica; ethyl acetate:petroleum ether 60-80/1:4).

Yield 76%.

1H-NMR (CDCl$_3$): 0.80-2.17 ppm, m, 10.0 H (cyclohexyl H); 3.88 ppm, d, J=5.4 Hz, 2.0 H (phenoxy-CH$_2$); 3.92 ppm, d, J=5.8 Hz, 2.0 H (CH$_2$ONO$_2$); 6.87-7.95 ppm, m, 4.0 H (arom. H); 10.53 ppm, s, 1.0 H (CH).

EXAMPLE XXIV 3,5-Diethoxycarbonyl-2,6-dimethyl-4-[2-[(4-nitroxymethyl-(trans)-cyclohexyl)methoxy]phenyl]-1,4-dihydropyridine A solution of 3.3 g of the compound from Example XXIVc and 4.4 g of ethyl 3-aminocrotonate was refluxed for 26 hours. The title compound was purified by chromatography (silica; ethyl acetate:petroleum ether 60-80/1:3) and crystallized from methanol at −20° C.

Yield 20%.

Empirical formula C$_{27}$H$_{36}$N$_2$O$_8$.

Molecular weight 516.

Melting point 78°-80° C.

TLC system: ethyl acetate:petroleum ether 60-80/1:2.

R$_f$ 0.60.

NMR data: (CDCl$_3$): 0.88-1.37 ppm, m, 9.0 H (2×ester-CH$_3$, 3×cyclohexyl-H); 3.51-2.17 ppm, m, 7.0 H (7×cyclohexyl-H); 2.26 ppm, s, 6.0 H (2×CH$_3$); 3.73 ppm, d, J=6.0 Hz, 2.0 H (phenoxy-CH$_2$); 4.03 ppm, q, J=7.0 Hz, 4.0 H (2×ester-CH$_2$); 4.31 ppm, d, J=5.8 Hz, 2.0 H (CH$_2$ONO$_2$); 5.25 ppm, s, 1.0 H (CH); 5.56 ppm, bs, 0.9 H (NH); 6.65-7.32 ppm, m, 4.0 H (arom. H).

Example XXXVa

10-Bromodecanol

A solution of 50 g of decane-1,10-diol in 300 ml of 48% aqueous hydrobromic acid was heated at 90° C. for 24 hours while the solution was extracted continuously with petroleum ether 100-140. After cooling to room temperature, the petroleum ether solution was evaporated and the residue was purified by distillation. Boiling point 121°-124° C. (0.1 mm Hg).

Yield 69%.

1H-NMR (CDCl$_3$): 0.98-2.20 ppm, m, 16.0 H (C-(CH$_2$)$_8$COH); 3.43 ppm, t, J=6.9 Hz, 2.0 H (OCH$_2$); 3.65 ppm, t, J=6.2 Hz, 1.9 H (BrCH$_2$).

Example XXXVb 2-(10-Hydroxydecyloxy)benzaldehyde

A mixture of 12.2 g of salicylaldehyde, 23.7 g of the compound from Example XXVa and 6.6 g of potassium hydroxide in 100 ml of dimethyl sulfoxide was heated at 140° C. for 4 hours, with stirring. After cooling to room temperature, the solution was diluted with water and extracted with ethyl acetate. The organic solution was dried over magnesium sulfate and evaporated. The residue was purified by chromatography (silica; dichloromethane).

Yield 44%.

1H-NMR (CDCl$_3$): 1.20-2.00 ppm, m, 17.0 H (C-(CH$_2$)$_8$COH); 3.66 ppm, t, J=6.1 Hz, 2.0 H (hydroxy-CH$_2$); 4.09 ppm, t, J=6.5 Hz, 2.0 H (phenoxy-CH$_2$); 6.90-7.95 ppm, m, 4.0 H (arom. H); 10.52 ppm, s, 1.0 H (CH).

Example XXVc 2-(10-Nitroxydecyloxy)benzaldehyde

A mixture of 5.0 ml of nitric acid and 12.1 ml of acetic anhydride was added at 0° C. to a solution of 11.0 g of the compound from Example XXVb in ethyl acetate. After everything had been added, the solution was stirred for a further 15 minutes and then poured into water. This mixture was stirred for 1 hour and then extracted with ethyl acetate. The organic solution was washed with aqueous sodium carbonate, dried over magnesium sulfate and evaporated. The residue was purified by chromatography (silica; ethyl acetate:petroleum ether 60-80/1:4).

Yield 75%.

1H-NMR (CDCl$_3$): 0.80-2.23 ppm, m, 16.0 H (C-(CH$_2$)$_8$C); 4.10 ppm, t, J=6.1 Hz, 2.0 H (phenoxy-CH$_2$); 4.46 ppm, t, J=6.5 Hz, 2.0 H (CH$_2$ONO$_2$); 6.92-7.92 ppm, m, 4.0 H (arom. H); 10.53 ppm, s, 1.0 H (CHO).

Example XXV 3,5-Diethoxycarbonyl-2,6-dimethyl-4-[2-(10-nitroxydecyloxy)phenyl]-1,4-dihydropyridine Prepared from 4.0 g of the compound from Example XXVc and 4.0 g of ethyl 3-aminocrotonate as described in Example XXI. Crystallized from ethyl acetate/petroleum ether 60-80.

Yield 20%.

Empirical formula C$_{29}$H$_{42}$N$_2$O$_8$.

Molecular weight 546.

Melting point 91°-93° C.

TLC system: ethyl acetate: petroleum ether 60-80/1:3.

R$_f$ 0.33.

NMR data: (CDCl$_3$): 1.02-2.00 ppm, m, 22.0 H (OC(CH$_2$)$_8$CO, 2×ester-CH$_3$, J=7.0 Hz); 2.27 ppm, s, 6.0 H (2×CH$_3$); 3.78-4.21 ppm, m, 6.0 H (phenoxy-CH$_2$, 2×ester-CH$_2$, J=7.0 Hz); 4.47 ppm, t, J=6.5 Hz, 2.0 H (CH$_2$ONO$_2$); 5.22 ppm, s, 1.0 H (CH); 5.63 ppm, bs, 0.9 H (NH); 6.67-7.39 ppm, m, 4.0 H (arom. H).

The following compounds according to the invention are synthesized by using essentially the same procedures as described above, from known or herein before described starting materials or from starting materials which can be made in a manner known to the expert:

Example XXVI 2,6-Dimethyl-3-ethoxycarbonyl-5-methoxycarbonyl-4-[2-(3-nitroxypropoxy)phenyl]-1,4-dihydropyridine Melting point: 112°–115° C.

Example XXVII 3,5-Dimethoxycarbonyl-2,6-dimethyl-4-[2-(3-nitroxypropoxy)phenyl]-1,4, -dihydropyridine Melting point: 109°–111° C.

Example XXVIII 2,6-Dimethyl-3,5-diethoxycarbonyl-4-[2-(3-nitroxypropoxy)phenyl-1,4-dihydropyridine Melting point: 105°–107° C.

Example XXIX 2,6-Dimethyl-3-ethoxycarbonyl-5-methoxycarbonyl-4-[2-(4-nitroxybutoxy)phenyl]-1,4-dihydropyridine×2-$H_2O$ Melting point: 63°–65° C.

Example XXX 3,5-Dimethoxycarbonyl-2,6-dimethyl-4-[2-(6-nitroxyhexyloxy)phenyl]-1,4-dihydropyridine Melting point: 102°–103° C.

Example XXXI 2,6-Dimethyl-3-methyloxycarbonyl-5-methyloxycarbonyl-4-[2-(nitroxyhexyloxyphenyl)]-1,4-dihydropyridine NMR data ($CDCl_3$): 0.37–2.07 ppm, m, 26.0 H (C-$(CH_2)_4$-C, menthyl-H); 2.16–2.40 ppm, m, 6.0 H (2,6-di-$CH_3$); 3.57–3.66 ppm, m, 3.0 H ($OCH_3$); 3.93 ppm, t, $J = 6.3$ Hz, 2.0 H (phenoxy-$CH_2$); 4.37–4.86 ppm, m, 3.0 H ($CH_2ONO_2$, $CO_2CH$); 5.22 ppm, bs, 1.0 H (CH); 5.59 ppm, bs, 1.0 H (NH); 6.68–7.32 ppm, m, 4.0 (arom. H).

Example XXXII 3,5-Dimethoxycarbonyl-2,6-dimethyl-4-{2-[4-nitroxymethyl(trans)cyclohexylmethoxy]phenyl}-1,4-dihydropyridine Melting point: 158°–160° C.

Example XXXIII 3,5-Dimethoxycarbonyl-2,6-dimethyl-4-{2-[2-nitroxypropyloxy)phenyl}-1,4-dihydropyridine Melting point: 127°–131° C.

Example XXXIV 3,5-Dimethoxycarbonyl-2,6-dimethyl-4-{3-[4-nitroxymethyl(trans)cyclohexylmethoxy]phenyl}-1,4-dihydropyridine Melting point: 184°–188° C.

Example XXXV 2,6-Dimethyl-3,5-dimethoxycarbonyl-4-[2-(8-nitroxyoctyloxy)phenyl]-1,4-dihydropyridine Melting point: 116°–119° C.

Example XXXVI 3,5-Dimethoxycarbonyl-2,6-dimethyl-4-[2-(14-nitroxytetradecyloxy)phenyl]-1,4-dihydropyridine Melting point: 99°–102° C.

Example XXXVII 3,5-Dimethoxycarbonyl-2,6-dimethyl-4-[2-(2-nitroxycyclohexoxy)phenyl]-1,4-dihydropyridine×methanol Melting point: 73°–78° C.

Example XXXVIII

R-(−)-3,5-Dimethoxycarbonyl(2,6-dimethyl-4-[2-(2-methyl-3-nitroxypropoxy)phenyl]-1,4-dihydropyridine Melting point: 107°–109° C.

Pharmacology

The pharmacological activity of the compounds according to the invention was demonstrated in vivo in anesthetized rabbits and in vitro in the so-called rat aorta assay.

In the anesthetized rabbits, the decrease of arterial blood pressure and the effect on the heart rate, whereas they produce a marked decrease of the arterial blood pressure.

In the rat aorta assay, the compounds according to the invention are—in contrast to pure Ca-antagonists like nifedipine—able to effect an up to 100% relaxation of a contraction of the rat aorta induced by phenylephrine.

In the tables following the detailed description of the in vivo and in vitro experiments, the compounds investigated are identified by numbers which correspond to the numbers in the Examples.

Anesthetized Rabbit Experiments

Animals Anesthesia and Surgical Procedures

New Zealand white rabbits (2.5–3 kg) were anesthetized (30 mg×$kg^{-1}$ pentobarbitone, i.v., supplemetal doses as needed). Tracheotomy was performed, and an intra-tracheal cannula was inserted. No artificial ventilation was applied and body temperature was maintained at 37°–38° C.

Left ventricular pressure (LVP) was measured (millar Mikro-Tip catheter via the right carotid artery with transducer in the left ventricle). The LVP signal was differentiated electronically to obtain the rate of change of LVP (LV dP/dt). The heart rate (HR) was derived from the LVP pulse signal. The jugular vein was cannulated for infusion of the test compounds. Aortic blood pressure (SAP and DAP) was monitored (Gould-Statham pressure transducer) by inserting a polyethylene catheter filled with heparin (50 IU×$ml^{-1}$) through the femoral artery into the abdominal aorta. Heparin (150 IU×$kg^{-1}$, i.v.) was administered to prevent blood clotting.

After completion of surgical procedures, the rabbits were allowed to recover for 15 minutes before drug administration was started.

Infusion of Test Compounds and Test Protocol

Drugs were infused at constant rate (0.5 ml×$min^{-1}$) for 10 minutes at various doses, resulting in a typical dose range of 2.0, 20.0 and 200 μg×$kg^{-1}$×$min^{-1}$ (2.5 kg rabbit).

Due to poor solubility, 1 mg×ml$^{-1}$ solutions of all the compounds tested were prepared in Intralipid$^{(R)}$ 10%, containing 10% (v/v) dimethyl sulfoxide (DMSO). Infusion of this solvent at 0.5 ml×min$^{-1}$ in the anesthetized rabbit, as was performed at the aforementioned highest doese, did not lead to changes in hemodynamic state. At the infusion of lower doses, the 1 mg×ml$^{-1}$ stock solutions were diluted with Intralipid$^{(R)}$ 10%.

Definition of Effects

The presented data are based on the effects obtained at the end of the 10 min infusion period at the highest dose tested (150–200 μg×kg$^{-1}$'min$^{-1}$).

The indicated ratings are referring to the effects (decrease, defined as percentage of basal value before infusion of the drug) on arterial blood pressure as follows:

| | |
|---|---|
| No decrease or decrease less than 5% | Inactive |
| Decrease between 5 and 40% | Active |
| Decrease greater than 40% | Very Active |

TABLE I

Effects of the compounds according to the invention on the arterial blood pressure in the anesthetized rabbit.

| Example No. | Activity with regard to the lowering of blood pressure |
|---|---|
| I | Active* |
| VII | Very Active** |
| XV | Active |
| XVII | Active |
| XVIII | Active |
| XIX | Active |
| XX | Active |
| XXI | Very Active |
| XXII | Very Active |
| XXIII | Very Active |
| XXIV | Very Active |
| XXV | Very Active |
| XXVI | Very Active |
| XXVII | Very Active |
| XXVIII | Very Active |
| XXIX | Very Active |
| XXX | Very Active |
| XXXI | Active |
| XXXII | Very Active |
| XXXIII | Very Active |
| XXXV | Very Active |
| XXXVII | Very Active |
| XXXVIII | Very Active |

*Active: Decrease in blood pressure between 5 and 40%.
**Very Active: Decrease in blood pressure greater than 40%.

In Vitro Rat Aorta Assay

Strips of thoracial rat aortae (without aortic arch, helically cut; length 1–1.5 cm; width about 2 mm) were place in an organ bath [20 ml; Krebs Ringer medium bubbled with O$_2$/CO$_2$ (95/5%) at 37' C.]. A resting tension of 0.5 g was applied and the preparations were equilibrated during 100 min (fresh buffer solution every 20 min). The strips were isotonically contracted with 50 mM KCl (equimolar part of NaCl in buffer omitted) in the presence of 1.25 mM CaCl$_2$.

Drug-induced relaxation was tested at increasing concentration (half log steps), till maximal or full relaxation (corresponding to basal precontraction value of organ length) had been reached.

Responses were calculated as change in organ length relatively to maximal displacement by contraction, EC$_{50}$ values corresponding to the drug concentration at which residual contraction is 50% of maximum.

TABLE 2

Effects of the compounds according to the invention on the contracted rat aorta.

| Example No. | EC$_{50}$ (mean, μM) | S.D. | Range | N |
|---|---|---|---|---|
| VII | 0.0590 | 0.0260 | 0.03–0.1 | 8 |
| XIV | 0.0800 | 0.0140 | 0.06–0.1 | 4 |
| XV | 0.0850 | 0.0170 | 0.06–0.1 | 4 |
| XVII | 0.0880 | 0.0160 | 0.06–0.1 | 4 |
| XIX | 0.0800 | 0.0210 | 0.05–0.1 | 4 |
| XX | 0.0380 | 0.0160 | 0.01–0.05 | 4 |
| XXI | 0.0140 | 0.0051 | 0.009–0.02 | 5 |
| XXII | 0.0600 | 0.0290 | 0.03–0.1 | 5 |
| XXIII | 0.0280 | 0.0150 | 0.01–0.05 | 5 |
| XXIV | 0.0078 | 0.0020 | 0.005–0.01 | 6 |
| XXV | 0.0670 | 0.0660 | 0.006–0.02 | 12 |
| XXVI | 0.0120 | 0.0081 | 0.002–0.02 | 6 |
| XXVII | 0.0057 | 0.0022 | 0.004–0.01 | 6 |
| XXVIII | 0.0077 | 0.0029 | 0.002–0.01 | 6 |
| XXIX | 0.0026 | 0.0012 | 0.001–0.005 | 9 |
| XXX | 0.0090 | 0.0018 | 0.005–0.01 | 6 |
| XXXII | 0.0065 | 0.0021 | 0.003–0.01 | 6 |
| XXXIII | 0.0160 | 0.0080 | 0.01–0.03 | 5 |
| XXXV | 0.0050 | 0.0031 | 0.002–0.01 | 4 |
| XXXVII | 0.0680 | 0.0250 | 0.03–0.1 | 4 |
| XXXVIII | 0.0750 | 0.0740 | 0.02–0.2 | 4 |

EC$_{50}$ = Concentration (μM) at which residual contraction is 50% of maximum;
S.D. = Standard deviation
N = Number of rat aortas tested

We claim:

1. A compound of the general formula 1,

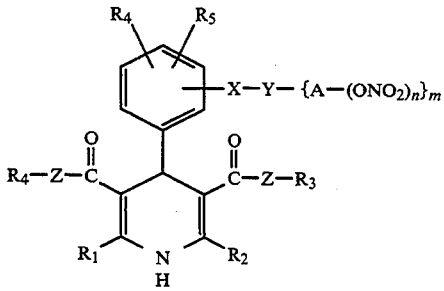

wherein

R$_1$ represents a lower alkyl group,

R$_2$ represents a lower alkyl group or —CH$_2$—S—CH$_2$—CH$_2$—NH$_2$,

R$_3$ and R$_4$ independently represent a lower alkyl, cycloalkyl or bicycloalkyl group, R$_5$ and R$_6$ independently represent H, a lower, optionally branched alkyl group, a lower, optionally branched alkoxy group, CN, NO$_2$, F, Cl or Br, X represents O, NH, CO, —O(CH$_2$)$_p$—CO— or S, Y represents O, N, NH, S, CO, CONH, CO$_2$ or a bond, with the provisos that X and Y do not at the same time represent O and-/or S, Y does not represent O, NH or S, when X is NH, Y does not represent CO, CO$_2$ or CONH, when X is CO, and Y does not represent N, NH, CONH or CO$_2$, when X is O, A represents an optionally branched 2–15C-alkylene group, a methylene cyclohexylene-methylene group, a cyclohexane-1,2-ylene group or a group of the formula [(CH$_2$)$_2$O]$_q$(CH$_2$)$_2$ wherein q is 1 or 2, n and m independently are 1, 2 or 3, Z represents O or NH and p is 1–6,
or a salt thereof.

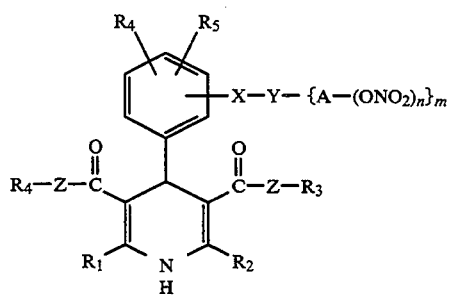

wherein the substituents and symbols have the meanings given in the specification, are new compounds with marked cardiovascular activity.

2. Compound of the formula 1 according to claim 1, wherein
 $R_1$ represents a 1–4C-alkyl group,
 $R_2$ represents a 1–4C-alkyl group,
 $R_3$ and $R_4$ independently represent a 1–4C-alkyl group or a menthyl group,
 $R_5$ represents H, 1–4C-alkoxy, $NO_2$, Cl or Br,
 $R_6$ represents H,
 X represents O, CO or $-O(CH_2)_p-CO-$,
 Y represents N, NH, CO or a bond,
 A represents an optionally branched 2–15C-alkylene group, a methylene cyclohexylene-methylene group, a cyclohexane-1,2-ylene group or a group of the formula $[(CH_2)_2O]_q(CH_2)_2$, wherein q is 1 or 2,
 n is 1,
 m is 1 or 2,
 Z represents O and
 p is 1,
or a salt thereof.

3. Compound of the formula 1 according to claim 1, wherein
 $R_1$ represents a 1–4C-alkyl group,
 $R_2$ represents a 1–4C-alkyl group,
 $R_3$ and $R_4$ independently represent a 1–4C-alkyl group or a menthyl group,
 $R_5$ represents H, 1–4C-alkoxy, $NO_2$, Cl or Br,
 $R_6$ represents H,
 X represents O,
 Y represents a bond,
 A represents an optionally branched 2–15C-alkylene group, a methylene cyclohexylene methylene group or a group of the formula $[(CH_2)_2O]_q(CH_2)_2$, wherein q is 2,
 n is 1,
 m is 1 and
 Z represents O,
or a salt thereof.

4. A pharmaceutical composition comprising an effective amount of a compound claim 1 or of a pharmaceutically-acceptable salt thereof and a suitable carrier.

5. A method for lowering block pressure or treating a heart disease, which comprises administering an effective amount of a compound of claim 1 or of a pharmaceutically-acceptable salt thereof to a mammal in need of such therapy.

* * * * *

UNITED STATES PATENT AND TRADEMARK OFFICE
CERTIFICATE OF CORRECTION

PATENT NO. : 5,378,718
DATED : January 3, 1995
INVENTOR(S) : Jan BRON, Geert J. STERK, Hendrik TIMMERMAN, Jan F. VAN DER WERF It is certified that error appears in the above-indentified patent and that said Letters Patent is hereby corrected as shown below:

```
Column 25, lines 3 to 15, delete entire text;
lines 16 to 18, delete "wherein...activity.";
line 19, "Compound" should read --A compound--.
Column 26, line 6, "Compound" should read --A
compound--; line 11, delete "or a menthyl
group"; line 28, "block" should read --blood--.
```

Signed and Sealed this

Fourteenth Day of March, 1995

Attest:

BRUCE LEHMAN

Attesting Officer          Commissioner of Patents and Trademarks